(12) United States Patent
Li et al.

(10) Patent No.: US 9,309,527 B2
(45) Date of Patent: Apr. 12, 2016

(54) PROTEIN IPA1 RELATED TO PLANT ARCHITECTURE, ITS CODING GENES AND USES

(75) Inventors: Jiayang Li, Beijing (CN); Qian Qian, Zhejiang (CN); Yonghong Wang, Beijing (CN); Yongqing Jiao, Beijing (CN); Dawei Xue, Zhejiang (CN); Guifu Liu, Beijing (CN); Jing Wang, Beijing (CN); Guojun Dong, Zhejiang (CN)

(73) Assignee: Institute of Genetics and Developmental Biology, Chinese Academy of Sciences, Beijing (CN)

( * ) Notice: Subject to any disclaimer, the term of this patent is extended or adjusted under 35 U.S.C. 154(b) by 653 days.

(21) Appl. No.: 13/635,052

(22) PCT Filed: Mar. 31, 2011

(86) PCT No.: PCT/CN2011/000558
§ 371 (c)(1),
(2), (4) Date: Nov. 28, 2012

(87) PCT Pub. No.: WO2011/127744
PCT Pub. Date: Oct. 20, 2011

(65) Prior Publication Data
US 2013/0091597 A1    Apr. 11, 2013

(30) Foreign Application Priority Data
Apr. 12, 2010 (CN) .......................... 2010 1 0146613

(51) Int. Cl.
*C07K 14/415* (2006.01)
*C12N 15/29* (2006.01)
*C12N 15/82* (2006.01)
*A01H 1/00* (2006.01)
*A01H 1/04* (2006.01)

(52) U.S. Cl.
CPC .............. *C12N 15/8243* (2013.01); *A01H 1/04* (2013.01); *C07K 14/415* (2013.01); *C12N 15/8261* (2013.01)

(58) Field of Classification Search
None
See application file for complete search history.

(56) References Cited

U.S. PATENT DOCUMENTS

2006/0123505 A1* 6/2006 Kikuchi et al. ............... 800/278

FOREIGN PATENT DOCUMENTS

| CN | 101415829 A | 4/2009 |
| CN | 101921321 A | 12/2010 |

OTHER PUBLICATIONS

Xie et al. Plant Physiol. 142, 280-293 (2006).*
Guo et al (2004, Proc. Natl. Acad. Sci. USA 101: 9205-9210).*
Toki et al. (Plant Physiol. (1992) 100, 1503-1507).*
GenBank accession No. AK107191, Dec. 4, 2008 [retrieved on May 21, 2011], Retrieved from NCBI [online]: <URL:http://www.ncbi.nlm.nih.gov/nuccore/AK107191.
Xie et al., "Genomic organization, differential expression, and interaction of SQUAMOSA promoter-binding-like transcription factors and micro RNA156 in rice", Plant Physiology, vol. 142, pp. 280-293 (Sep. 2006).
Mao et al., "Regulation of OsSPL14 by OsmiR156 defines ideal plant in rice", Nature Genetics, vol. 42, No. 6, pp. 541-544 (May 23, 2010).

* cited by examiner

*Primary Examiner* — Anne Kubelik
*Assistant Examiner* — Charles Logsdon
(74) *Attorney, Agent, or Firm* — Drinker Biddle & Reath LLP

(57) ABSTRACT

The present invention discloses a protein IPA1 related to plant architecture, its coding genes and uses, wherein the protein is 1) or 2) as follows: 1) the protein consisting of the amino acid sequence showed by sequence 1 in the sequence list; 2) the protein derived from the protein of 1) by substitution and/or deletion and/or addition of one or several amino acid residues in the amino acid sequence defined in 1) and relating to plant architecture. IPA1 gene can be used for molecular marker-assisted breeding, cultivating new rice varieties and improving rice yield.

4 Claims, 4 Drawing Sheets

```
ttccgtctctttcctctctcttctctctccccctctcctggaggagagagaggagaagaggagggggggccgcgccaaga 80 gccacgcgcgctacagtctccttcccacccgcgaccgcgagcaATGGAGATGGCCAGTGGAGGAGGCGCCGCCGCCGCCG 160
                                           M  E  M  A  S  G  G  G  A  A  A  A CCGGCGGCGGAGTAGGCGGCAGCGGCGGCGGTGGTGCTGGAGGGGACGAGCACCGGCAGCTGCACGGTCTCAAGTTCGGC 240
 A  G  G  V  G  G  S  G  G  G  G  G  G  D  E  H  R  Q  L  H  G  L  K  F  G AAGAAGATCTACTTCGAGGACGCCGCCGCGGCAGCAGGCGGCGGCGGCACTGGCAGTGGCAGTGGCAGCGCGAGCGCCGC 320
 K  K  I  Y  F  E  D  A  A  A  A  G  G  G  T  G  S  G  S  G  S  A  S  A  A GCCGCCGTCCTCGTCTTCCAAGGCGGCGGGTGGTGGACGCGGCGGAGGGGGCAAGAACAAGGGGAAGGGCGTGGCCGCGG 400
 P  P  S  S  S  S  K  A  A  G  G  G  R  G  G  G  K  N  K  G  K  G  V  A  A CGGCGCCACCGCCGCCGCCGCCGCCGCGGTGCCAGCTGGAGGGGTGCGGCGCGGATCTGAGCGGGATCAAGAACTAC 480
 A  A  P  P  P  P  P  P  P  P  R  C  Q  V  E  G  C  G  A  D  L  S  G  I  K  N  Y TACTGCCGCCACAAGGTGTGCTTCATGCATTGCAAGGCTCCCCGCGTCGTCGTCGCCGGCCTCGAGCAGCGCTTCTGCCA 560
 Y  C  R  H  K  V  C  F  M  H  S  K  A  P  R  V  V  V  A  G  L  E  Q  R  F  C GCAGTGCAGCAGGTTCCACCTGCTGCCTGAATTTGACCAAGGAAAACGCAGCTGCCGCAGACGCCTTGCAGGTCATAATG 640
 Q  C  S  R  F  H  L  L  P  E  F  D  Q  G  K  R  S  C  R  R  R  L  A  G  H  N AGCGCCGGAGGAGGCCGCAAACCCCTTTGGCATCACGCTACGGTCGACTAGCTGCATCTGTTGGTGAGCATCGCAGGTTC 720
 E  R  R  R  R  P  C  T  P  L  A  S  R  Y  G  R  L  A  A  S  V  G  E  H  R  R  F AGAAGCTTTACGTTGGATTTCTCCTACCCAAGGGTTCCAAGCAGCGTAAGGAATGCATGGCCAGCAATTCAACCAGGCGA 800
 R  S  F  T  L  D  F  S  Y  P  R  V  P  S  S  V  R  N  A  W  P  A  I  Q  P  G  D TCGGATCTCCGGTGGTATCCAGTGGCACAGGAACGTAGCTCCTCATGGTCACTCTAGTGCAGTGGCGGGATATGGTGCCA 880
 R  I  S  G  G  I  Q  W  H  R  N  V  A  P  E  G  H  S  S  A  V  A  G  Y  G  A ACACATACAGCGCCAAGGTAGCTCTTCTTCAGGGCCACCGGTGTTCGCTGGCCCAAATCTCCCTCCAGGTGGATGTCTC 960
 N  I  Y  S  G  Q  G  S  S  S  S  G  P  P  V  F  A  G  P  N  L  P  P  G  G  C  L GCAGGGTCGGTGCCGCCACCGACTCGAGCTGTGCTCTCTCTCTTCTGTCAACCCAGCCATGGGATACTACTACCCACAG 1040
                                ********************
 A  G  V  G  A  A  T  D  S  S  C  A  L  S  L  L  S  T  Q  P  W  D  T  T  T  H  S
 λ (Shaoniejing)
 I (Shaoniejing)

TGCCGCTGCCAGCCACAACCAGGCTGCAGCCATGTCCACTACCACCAGCTTTGATGGCAATCCTGTGGCACCCTCCGCCA 1120
 A  A  A  S  H  N  Q  A  A  A  M  S  T  T  T  S  F  D  G  N  P  V  A  P  S  A

TGGCGGGTAGCTACATGGCACCAAGCCCCTGGACAGGTTCTCGGGGCCATGAGGGTGGTGGTCGGAGCGTGGCGCACCAG 1200
 M  A  G  S  Y  M  A  P  S  P  W  T  G  S  R  G  H  E  G  G  G  R  S  V  A  H  Q

CTACCACATGAAGTCTCACTTGATGAGGTGCACCCTGGTCCTAGCCATCATGCCCACTTCTCCGGTGAGCTTGAGCTTGC 1280
 L  P  H  E  V  S  L  D  E  V  H  P  G  P  S  H  H  A  H  F  S  G  E  L  E  L  A

TCTGCAGGGAACGGTCCAGCCCCAGCACCACGCATCGATCCTGGGTCCGGCAGCACCTTCGACCAAACCAGCAACACGA 1360
 L  Q  G  N  G  P  A  P  A  P  R  I  D  P  G  S  G  S  T  F  D  Q  T  S  N  T

TGGATTGGTCTCTGTAGaggctgttccagctgccatcgatctgtcgtcccgcaaggcgagtcatggaactgaagaacctc 1440
 M  D  W  S  L  * atgctgcctgccctattttgtgttcaaattttccttccagtatggaaaggaaattctaaggtgactggcgattaetct 1520 ccctgtgatgaataataatgcgcgccttgaactcaattaattgctgtgccgcatccatctatgtaactctccatgaatt 1600 tttaagtatcagtgttaatgctgt 1624
```

Fig.3

SEQUENCE LISTING

<160> NUMBER OF SEQ ID NOS: 24

<210> SEQ ID NO 1
<211> LENGTH: 417
<212> TYPE: PRT
<213> ORGANISM: Oryza sativa

<400> SEQUENCE: 1

-continued

```
Met Glu Met Ala Ser Gly Gly Ala Ala Ala Ala Gly Gly Gly
1               5                   10                  15
Val Gly Gly Ser Gly Gly Gly Gly Gly Asp Glu His Arg Gln
            20              25              30
Leu His Gly Leu Lys Phe Gly Lys Lys Ile Tyr Phe Glu Asp Ala Ala
        35              40                  45
Ala Ala Ala Gly Gly Gly Thr Gly Ser Gly Ser Gly Ser Ala Ser
50                      55              60
Ala Ala Pro Pro Ser Ser Ser Lys Ala Gly Gly Gly Arg Gly
65              70              75              80
Gly Gly Gly Lys Asn Lys Gly Lys Gly Val Ala Ala Ala Pro Pro
                85              90              95
Pro Pro Pro Pro Pro Pro Arg Cys Gln Val Glu Gly Cys Gly Ala Asp
            100             105             110
Leu Ser Gly Ile Lys Asn Tyr Tyr Cys Arg His Lys Val Cys Phe Met
        115             120             125
His Ser Lys Ala Pro Arg Val Val Ala Gly Leu Glu Gln Arg Phe
    130             135             140
Cys Gln Gln Cys Ser Arg Phe His Leu Leu Pro Glu Phe Asp Gln Gly
145             150             155             160
Lys Arg Ser Cys Arg Arg Leu Ala Gly His Asn Glu Arg Arg
            165             170             175
Arg Pro Gln Thr Pro Leu Ala Ser Arg Tyr Gly Arg Leu Ala Ala Ser
            180             185             190
Val Gly Glu His Arg Arg Phe Arg Ser Phe Thr Leu Asp Phe Ser Tyr
        195             200             205
Pro Arg Val Pro Ser Ser Val Arg Asn Ala Trp Pro Ala Ile Gln Pro
    210             215             220
Gly Asp Arg Ile Ser Gly Gly Ile Gln Trp His Arg Asn Val Ala Pro
225             230             235             240
His Gly His Ser Ser Ala Val Ala Gly Tyr Gly Ala Asn Thr Tyr Ser
            245             250             255
Gly Gln Gly Ser Ser Ser Gly Pro Pro Val Phe Ala Gly Pro Asn
        260             265             270
Leu Pro Pro Gly Gly Cys Leu Ala Gly Val Gly Ala Ala Thr Asp Ser
    275             280             285
Ser Cys Ala Leu Ser Leu Leu Ser Thr Gln Pro Trp Asp Thr Thr Thr
    290             295             300
His Ser Ala Ala Ala Ser His Asn Gln Ala Ala Ala Met Ser Thr Thr
305             310             315             320
Thr Ser Phe Asp Gly Asn Pro Val Ala Pro Ser Ala Met Ala Gly Ser
            325             330             335
Tyr Met Ala Pro Ser Pro Trp Thr Gly Ser Arg Gly His Glu Gly Gly
            340             345             350
Gly Arg Ser Val Ala His Gln Leu Pro His Glu Val Ser Leu Asp Glu
        355             360             365
Val His Pro Gly Pro Ser His His Ala His Phe Ser Gly Glu Leu Glu
    370             375             380
Leu Ala Leu Gln Gly Asn Gly Pro Ala Pro Arg Ile Asp Pro
385             390             395             400
Gly Ser Gly Ser Thr Phe Asp Gln Thr Ser Asn Thr Met Asp Trp Ser
            405             410             415
```

Leu

<210> SEQ ID NO 2
<211> LENGTH: 1624
<212> TYPE: DNA
<213> ORGANISM: Oryza sativa
<220> FEATURE:
<221> NAME/KEY: CDS
<222> LOCATION: (124)..(1374)

<400> SEQUENCE: 2

```
ttccgtctct ttcctctctc ttctctctcc ccctctcctg gaggagagag aggagaagag      60 gaggggggc cgcgccaaga gccacgcgcg ctacagtctc cttcccaccc gcgaccgcga      120 gca atg gag atg gcc agt gga gga ggc gcc gcc gcc gcc gcc ggc ggc      168
    Met Glu Met Ala Ser Gly Gly Gly Ala Ala Ala Ala Ala Gly Gly
    1               5                   10                  15 gga gta ggc ggc agc ggc ggc ggt ggt ggt gga ggg gac gag cac cgc      216
Gly Val Gly Gly Ser Gly Gly Gly Gly Gly Gly Asp Glu His Arg
            20                  25                  30 cag ctg cac ggt ctc aag ttc ggc aag aag atc tac ttc gag gac gcc      264
Gln Leu His Gly Leu Lys Phe Gly Lys Lys Ile Tyr Phe Glu Asp Ala
        35                  40                  45 gcc gcg gca gca ggc ggc ggc act ggc agt ggc agt ggc agc gcg          312
Ala Ala Ala Ala Gly Gly Gly Thr Gly Ser Gly Ser Gly Ser Ala
    50                  55                  60 agc gcc gcg ccg ccg tcc tcg tct tcc aag gcg gcg ggt ggt gga cgc      360
Ser Ala Ala Pro Pro Ser Ser Ser Lys Ala Ala Gly Gly Gly Arg
65                  70                  75 ggc gga ggg ggc aag aac aag ggg aag ggc gtg gcc gcg gcg gcg cca      408
Gly Gly Gly Gly Lys Asn Lys Gly Lys Gly Val Ala Ala Ala Ala Pro
80              85                  90                  95 ccg ccg ccg ccg ccg ccg ccg cgg tgc cag gtg gag ggg tgc ggc gcg      456
Pro Pro Pro Pro Pro Pro Pro Arg Cys Gln Val Glu Gly Cys Gly Ala
                100                 105                 110 gat ctg agc ggg atc aag aac tac tac tgc cgc cac aag gtg tgc ttc      504
Asp Leu Ser Gly Ile Lys Asn Tyr Tyr Cys Arg His Lys Val Cys Phe
        115                 120                 125 atg cat tcc aag gct ccc cgc gtc gtc gtc gcc ggc ctc gag cag cgc      552
Met His Ser Lys Ala Pro Arg Val Val Val Ala Gly Leu Glu Gln Arg
    130                 135                 140 ttc tgc cag cag tgc agc agg ttc cac ctg ctg cct gaa ttt gac caa      600
Phe Cys Gln Gln Cys Ser Arg Phe His Leu Leu Pro Glu Phe Asp Gln
145                 150                 155 gga aaa cgc agc tgc cgc aga cgc ctt gca ggt cat aat gag cgc cgg      648
Gly Lys Arg Ser Cys Arg Arg Arg Leu Ala Gly His Asn Glu Arg Arg
160                 165                 170                 175 agg agg ccg caa acc cct ttg gca tca cgc tac ggt cga cta gct gca      696
Arg Arg Pro Gln Thr Pro Leu Ala Ser Arg Tyr Gly Arg Leu Ala Ala
                180                 185                 190 tct gtt ggt gag cat cgc agg ttc aga agc ttt acg ttg gat ttc tcc      744
Ser Val Gly Glu His Arg Arg Phe Arg Ser Phe Thr Leu Asp Phe Ser
        195                 200                 205 tac cca agg gtt cca agc agc gta agg aat gca tgg cca gca att caa      792
Tyr Pro Arg Val Pro Ser Ser Val Arg Asn Ala Trp Pro Ala Ile Gln
    210                 215                 220 cca ggc gat cgg atc tcc ggt ggt atc cag tgg cac agg aac gta gct      840
Pro Gly Asp Arg Ile Ser Gly Gly Ile Gln Trp His Arg Asn Val Ala
225                 230                 235 cct cat ggt cac tct agt gca gtg gcg gga tat ggt gcc aac aca tac      888
Pro His Gly His Ser Ser Ala Val Ala Gly Tyr Gly Ala Asn Thr Tyr
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 240 |     |     |     |     | 245 |     |     |     |     | 250 |     |     |     |     | 255 |     |

```
agc ggc caa ggt agc tct tct tca ggg cca ccg gtg ttc gct ggc cca      936
Ser Gly Gln Gly Ser Ser Ser Ser Gly Pro Pro Val Phe Ala Gly Pro
            260                 265                 270 aat ctc cct cca ggt gga tgt ctc gca ggg gtc ggt gcc gcc acc gac      984
Asn Leu Pro Pro Gly Gly Cys Leu Ala Gly Val Gly Ala Ala Thr Asp
        275                 280                 285 tcg agc tgt gct ctc tct ctt ctg tca acc cag cca tgg gat act act     1032
Ser Ser Cys Ala Leu Ser Leu Leu Ser Thr Gln Pro Trp Asp Thr Thr
    290                 295                 300 acc cac agt gcc gct gcc agc cac aac cag gct gca gcc atg tcc act     1080
Thr His Ser Ala Ala Ala Ser His Asn Gln Ala Ala Ala Met Ser Thr
305                 310                 315 acc acc agc ttt gat ggc aat cct gtg gca ccc tcc gcc atg gcg ggt     1128
Thr Thr Ser Phe Asp Gly Asn Pro Val Ala Pro Ser Ala Met Ala Gly
320                 325                 330                 335 agc tac atg gca cca agc ccc tgg aca ggt tct cgg ggc cat gag ggt     1176
Ser Tyr Met Ala Pro Ser Pro Trp Thr Gly Ser Arg Gly His Glu Gly
            340                 345                 350 ggt ggt cgg agc gtg gcg cac cag cta cca cat gaa gtc tca ctt gat     1224
Gly Gly Arg Ser Val Ala His Gln Leu Pro His Glu Val Ser Leu Asp
        355                 360                 365 gag gtg cac cct ggt cct agc cat cat gcc cac ttc tcc ggt gag ctt     1272
Glu Val His Pro Gly Pro Ser His His Ala His Phe Ser Gly Glu Leu
    370                 375                 380 gag ctt gct ctg cag ggg aac ggt cca gcc cca gca cca cgc atc gat     1320
Glu Leu Ala Leu Gln Gly Asn Gly Pro Ala Pro Ala Pro Arg Ile Asp
385                 390                 395 cct ggg tcc ggc agc acc ttc gac caa acc agc aac acg atg gat tgg     1368
Pro Gly Ser Gly Ser Thr Phe Asp Gln Thr Ser Asn Thr Met Asp Trp
400                 405                 410                 415 tct ctg tagaggctgt tccagctgcc atcgatctgt cgtcccgcaa ggcgagtcat       1424
Ser Leu ggaactgaag aacctcatgc tgcctgccct tattttgtgt tcaaattttc ctttccagta    1484 tggaaggaa attctaaggt gactggcgat taatctccct gtgatgaata ataatgcgcg     1544
cccttgaact caattaattg ctgtgccgca tccatctatg taactctcca tgaattttta   1604
agtatcagtg ttaatgctgt                                                1624
```

<210> SEQ ID NO 3
<211> LENGTH: 7335
<212> TYPE: DNA
<213> ORGANISM: Oryza sativa

<400> SEQUENCE: 3

```
gcaatgtaga gccacgtagg caagtcgctt gcgtggagga gagagggag tggggaccgt      60 tcccaaccca gcttcgtgtg accaagtttg gccacacggg ccaaacgaac ctcagcaact    120
tttgtcagaa agaaagaac ctccgcgaga aacaagaaag cgagagaggg agagaaagga    180
ggctcgtcgg agtaggggcg ctcggggtat ggggctcggc ggaggctcgc tggagtaggg    240
gccgccactg cgtggggctc gccggagtag gggcgctcgg ggagcctccc gagatccgcc    300
gctcagcggc gccgccgtct tccgggcaga gctctcgaag ctcgccctcc tcgcgcgccg    360
gtggcgttgg cggggcccgc gtgtggctac gcagctccgg tgctgcgcct ccaccgtcga    420
cgacagcgcc gcttggcgct gccgccgtct tccgccgcgc cgctggacgc cgccagatct    480
gctgctcgtc gccgcgtggg ccgctccacc cggttggagg aggagaggcg gcgccgcgct    540
```

```
tgggctgccc caccgccgag ctctgccgcg ccgttcgccg gtgctgccga gctccgccgc    600
gcctgccgga gcacgctgcc atggccgccc tggagaagac acgagagaat taggtggagg    660 gtggggaag ggtgagattt tttatattat ctatgggtcc cattataaat tttctaaacc     720
acacttatac tgtgggtgca gtgtcattta gagttcccaa accacctatg ttgcagctgt    780
ggtataacaa tttgctagga cgcattgcta ctgcccttgt accctgctat aagaagataa    840
ccaatgacat ctccactcga ttttctcggc gcgcgtgtga gggtgtgagg ataattttta    900
ttttaagtgg ttttttaaggg cggagagaga gagagagaga gggcaccgca ctacttctac   960
ttgtgtgtgt gtcgctcgct gggcttcgcc acctttccgt ctctttcctc tctcttctct    1020
ctccccctct cctggaggag agagaggaga agaggagggg gggccgcgcc aagagccacg    1080
cgcgctacag tctccttccc acccgcgacc gcgagcaatg gagatggcca gtggaggagg    1140
cgccgccgcc gccgccggcg gcggagtagg cggcagcggc ggcggtggtg gtggagggga    1200
cgagcaccgc cagctgcacg gtctcaagtt cggcaagaag atctacttcg aggacgccgc    1260
cgcggcagca ggcggcggcg gcactggcag tggcagtggc agcgcgagcg ccgcgccgcc    1320
gtcctcgtct tccaaggcgg cgggtggtgg acgcggcgga ggggcaaga acaaggggaa     1380 gggcgtggcc gcggcggcgc caccgccgcc gccgccgccg ccgcggtgcc aggtggaggg    1440
gtgcggcgcg gatctgagcg ggatcaagaa ctactactgc cgccacaagg tgtgcttcat    1500
gcattccaag gctccccgcg tcgtcgtcgc cggcctcgag cagcgcttct gccagcagtg    1560
cagcaggtca ctctctcact cacctcgcca ttgctgatgt caccactgct tttgcttttgc   1620 tttgcttgct ctccctcctc tttcacctat ctctcttgtt tatttgcttc ttgttcttgt    1680
ttagtgctag tacatgtgtt gttattgttg tgccgttttg tcttttgggt tattgtgttg    1740
ttgttactac tcgttttact ataggttttt aaggtttatg agcacggcca ccacattaga    1800
tgcactgtca agtggtgtgt gtgggacctt tcctgctaaa acaagctgat ttcaactctc    1860
tgaaacttcc tgcatttcat ctattttat cttttgattgt gttgggagta ctacactagt    1920
agtgttaata ttttgactgg tgcttatgag atttttaagt tggtaggttg atgaggaaaa    1980
tactccttta tatggttgag tgatgtgact tgcctgtctg cctgcctgcc tgccgctttg    2040
cataagattc ctctgtgtta gtaagagcca ctgtttattt gtactggtgc ttactctact    2100
tagttaatta gccattagct ataaaattcc gttgatgttg caagcttagc aatgccacg     2160 gtaagaatgg gagagagaag ttggctaaag ctgttgcttt gtagtttgta ctatatatgt    2220
gtctttgtgt tgcaagatat gcaactccta ctatgctgtg acttgagctc aaggttttca    2280
gttatctata gatccttact actactgagc atactaccac ttctgtatgg tagcatatgg    2340
tagcatagtc caagttccaa cgcctcgcca gttgttcata atctatacta ccacttctgt    2400
gcatttgtta cttttattta atagtttgtc tcattagctg acaagcatat gcctgttttg    2460
atatctgccc ctcttgtaat agtctatgga tagcttggac tgtttgatgc tttaattttt    2520
tactagcaac acttagggcc cctttgaaat ggaggattag caaaggaatt ttggaggatt    2580 catttttccta aggattttt cctatagagc cctttgattc atagaaagag gataggaaaa    2640
cttccgtagg attgcattcc tatgatcaat tccataggaa aataagcaag aggttagacc    2700
tcttgtgaaa ctttcctttg ttgagtgtat cttgtggtat aatcaaaggg ctcttctctc    2760
catttcatgt gttttcaatt cctgtaggat tggaaaaaca tacaacttca attcctacgt    2820
ttttcctatt cctatgtttt tcctatcctg cgtttcaaag gggcccttaa ggatgaaggg    2880
aagtaagaga aacatactag agaatatgta gtagtatttc tacattccat atttgtagca    2940
```

```
ctagcccaca aatatctttg ccttgtactt acttcatacc agttcccccc ttttcagagc    3000
aaaccaacaa tttctgttgc cttatatatc tagtgtcttc gtactaatat atctgttcca    3060
aaatgtacct gtccaaattc atagctagaa atagctttat ttaggacgga agtaataact    3120
gttgttagag acttggttca gacttttggt tatgttgagg ctactatcat ttcctttacg    3180
ggccaaatta ctacaaatga gaattcataa aaatgtcaag attttatgat tgttgtagct    3240
ttatttagga cggaggtagt aattgttgtt agagacttgg ttcagacttt tggttacgtt    3300
gaagctacta tcatttcctt tatggtcaaa ttactaacaa tgagtattca taaaaatgtc    3360 aagatttat aattgagctg tgccagtgct aagtgtgtca ctatctgatg ccataatgca    3420
tcattataaa agccagatgg accattagct tttatgtgta ggacacctgc cgtccaatta    3480
gatggataac catctagtgt ttgtgtactg ttattttaag cccgacatct cacaactcca    3540
tgaatgatta cagtcttcct ttcacatggt gtccttttgt tgtgttagga atagcatttt    3600
ttatttatgg gtgtaattat gaaaggcact aggagagttg ctgctttatc ttgatgggat    3660
ttgtagtaat accatcttta ggatgacaag aaatcttgtt ctgagttagc atgggctgcc    3720
ttttgacctg agctacggtt tgctatgttt ggcttgcatc atgcagatct attaggataa    3780
taagcatata aaagttgctt gcattgtgca ttgcttgttt taccttgatt catgtaggag    3840
taatttgctc gccatgcctc gttttgcttt ctgagtcaac agccaaattt agatgatgta    3900
ccttctgttg cttcaaaaac tcagtcactg cacagcagca gtggatagga ttcagaatca    3960
atctatccat gattctctgt tcacataata tgacaggttc cacctgctgc ctgaatttga    4020
ccaaggaaaa cgcagctgcc gcagacgcct tgcaggtcat aatgagcgcc ggaggaggcc    4080
gcaaacccct ttggcatcac gctacggtcg actagctgca tctgttggtg gtatcatcag    4140
aggctcttgt tttctttgca tcttgtgtgt ttgttggtaa ctactggttg cattcgctga    4200
tgtgttgttt gttgcgattc ttgatccaga agagcatcgc aggttcagaa gctttacgtt    4260
ggatttctcc tacccaaggg ttccaagcag cgtaaggaat gcatggccag caattcaacc    4320
aggcgatcgg atctccggtg gtatccagtg gcacaggaac gtagctcctc atggtcactc    4380
tagtgcagtg gcgggatatg gtgccaacac atacagcggc caaggtagct cttcttcagg    4440
gccaccggtg ttcgctggcc caaatctccc tccaggtgga tgtctcgcag gggtcggtgc    4500
cgccaccgac tcgagctgtg ctctctctct tctgtcaacc cagccatggg atactactac    4560
ccacagtgcc gctgccagcc acaaccaggc tgcagccatg tccactacca ccagctttga    4620
tggcaatcct gtggcaccct ccgccatggc gggtagctac atggcaccaa gcccctggac    4680
aggttctcgg ggccatgagg gtggtggtcg gagcgtggcg caccagctac cacatgaagt    4740
ctcacttgat gaggtgcacc ctggtcctag ccatcatgcc cacttctccg gtgagcttga    4800
gcttgctctg caggggaacg gtccagcccc agcaccacgc atcgatcctg gtccggcag    4860 caccttcgac caaaccagca acacgatgga ttggtctctg tagaggctgt tccagctgcc    4920
atcgatctgt cgtcccgcaa ggcgagtcat ggaactgaag aacctcatgc tgcctgccct    4980
tattttgtgt tcaaattttc ctttccagta tggaaaggaa attctaaggt gactggcgat    5040
taatctccct gtgatgaata ataatgcgcg cccttgaact caattaattg ctgtgccgca    5100
tccatctatg taactctcca tgaattttta agtatcagtg ttaatgctgt attgtcgagg    5160
acttctgctc gatatgttat ttctcttatg ttgttcatca tgaatctttt tctgcttatt    5220
attctggtgc cggggttgtcc ttaccacaga agattcagtt tcggttggcg agagtaaaca    5280
```

```
ccttccctgg ttgtgacaaa agctccaacc ttttcacttc tcggcctgta tttgatcttc    5340
cccttctgac gctgttatac tacttttaag cctgtatgtt tccagccttc caggtgaagg    5400
gccatactga agagaaaaca tgctttcagg gtttgatgca ttgtgtactt tacaagtgta    5460
cttaagattt tgtacaattt atatatgtac ctgctctgct gctgagtatt gtaggaaaga    5520
atcagttcga agggcgtgtg ttcatgtaaa gtgagaccac atgcacagcg tggatttgca    5580
gcatgctctc tgcaccagtg gtgttctgtt gatgcctttg atgggctggc tgaggtgaga    5640
ggaggatgat ccatgttggc agcttcttca ctctgaaaaa taaaagagaa gaaatgttca    5700
gatttgcaga caagtggaga gcagtgatat attctacaat aaaacattac caccttgctt    5760
ttctgtgatg atagatactc catggaattt tgcatcaagc atctcttgtt ttccagccac    5820
tgtttgctgg gttgttgctt caatttcgtc ccaattgatt ggtcaccttt ggttgtgact    5880
tgagagcact gagcactgaa acttttgctg tcagcaggca atgcacctca tccatgtcac    5940
gacagaggga gagagcccac ataaatggcc aaagaggaca catacagtgg cactgatgca    6000
gtcattgcaa cataattgac atcatgctaa acagtggtgt aaccatatgt tagctagcct    6060
gtgatcagca acagtgatt atggatctta atgtcacatg caagatttga cacagttgta    6120
aaaccatcat tgcattgaag atagatccca gcaacaggtg tatgatgtat tgctagaatg    6180
aatcaaaaat atcagtgcca tcctaaacac agtactacca acttgaacag ttatcaccgt    6240
gattggaaaa cagaaatgta taattgcttt ggcgccatct gcttatcatt atcatatgtc    6300
gcagatcact tgttccattg acacgactct ttttcactgt gaggagaggc accttgattt    6360
ggacttttca agagctgtag caagggctcc tttgaagcct tctacatgga ggagcagagc    6420
ataccatatg cagaactgta aactcttcct gaagctttcc agttccaccc ttgtagcttt    6480
aagctgccgc aagagaatta tcatttctaa cattgagatg tgatactgaa atgtgaaagg    6540
tgattcgcag tataggtccc aaaatatcgt ttacagcaac ttgcaaatcc tgcatgatac    6600
agttaattca tcaaaatatt agaccattag tactacagtc tacaaatacc ccttaactga    6660
acatgtatga taaggacaag attctgaagc tccagtgcat caggaatcca acgcagtatg    6720
caaatcatta ctgaacaaga ttcctgcact tacagaatca tcacctgttg taacaaggac    6780
cattctttgt tgccccagac acagcgaatt aatggtcatc ttcatttggc ccaggacatt    6840
catttgccaa tgcttctgct gattcatact gaaaagggga caatgcgtcc aattttaaaa    6900
gcatggaaga tgctataaaa gatcacccta tttaaaatgc agagaaaacc aaagatccaa    6960
catgatatg taatcacaga ttcccaacag taatgccgtc cagtaggcag taggggcatg    7020
cacataaaca ctagtactat gtagagctga agcttatttc cagaatgaag ctgaccttgc    7080
aaccgcaata aaggcaatag tagtgttcat cgcgcagctt agccaatata ttttgcaaat    7140
cctgcaagaa taaacacagg tcaatctcgt cctttcagca aaatttgcag tcttgcataa    7200
gatttctcag ataaaaaagg aagtctagac aagaatatga aggaaagaat gtgcaaacat    7260
aagtatattc ataattcaaa gttcgagcta tttccattgt cacaacataa tatgtgtaac    7320
caatagctgg taagc                                                    7335
```

<210> SEQ ID NO 4
<211> LENGTH: 610
<212> TYPE: DNA
<213> ORGANISM: Oryza sativa

<400> SEQUENCE: 4

```
ccagccatgg gatactacta cccacagtgc cgctgccagc cacaaccagg ctgcagccat      60
```

```
gtccactacc accagctttg atggcaatcc tgtggcaccc tccgccatgg cgggtagcta    120
catggcacca agcccctgga caggttctcg gggccatgag ggtggtggtc ggagcgtggc    180
gcaccagcta ccacatgaag tctcacttga tgaggtgcac cctggtccta gccatcatgc    240
ccacttctcc ggtgagcttg agcttgctct gcagggggaac ggtccagccc cagcaccacg   300
catcgatcct gggtccggca gcaccttcga ccaaaccagc aacacgatgg attggtctct    360
gtagaggctg ttccagctgc catcgatctg tcgtcccgca aggcgagtca tggaactgaa    420
gaacctcatg ctgcctgccc ttattttgtg ttcaaatttt cctttccagt atggaaagga    480
aattctaagg tgactggcga ttaatctccc tgtgatgaat aataatgcgc gcccttgaac    540
tcaattaatt gctgtgccgc atccatctat gtaactctcc atgaattttt aagtatcagt    600
gttaatgctg                                                          610

<210> SEQ ID NO 5
<211> LENGTH: 610
<212> TYPE: DNA
<213> ORGANISM: Oryza sativa

<400> SEQUENCE: 5
cagcattaac actgatactt aaaaattcat ggagagttac atagatggat gcggcacagc     60
aattaattga gttcaagggc gcgcattatt attcatcaca gggagattaa tcgccagtca    120
ccttagaatt tcctttccat actggaaagg aaaatttgaa cacaaaataa gggcaggcag    180
catgaggttc ttcagttcca tgactcgcct gcgggacga cagatcgatg gcagctggaa     240
cagcctctac agagaccaat ccatcgtgtt gctggtttgg tcgaaggtgc tgccggaccc    300
aggatcgatg cgtggtgctg gggctggacc gttcccctgc agcaagct caagctcacc      360 ggagaagtgg gcatgatggc taggaccagg gtgcacctca tcaagtgaga cttcatgtgg    420
tagctggtgc gccacgctcc gaccaccacc ctcatggccc cgagaacctg tccaggggct    480
tggtgccatg tagctacccg ccatggcgga gggtgccaca ggattgccat caaagctggt    540
ggtagtggac atggctgcag cctggttgtg gctggcagcg gcactgtggg tagtagtatc    600
ccatggctgg                                                          610

<210> SEQ ID NO 6
<211> LENGTH: 1624
<212> TYPE: DNA
<213> ORGANISM: Oryza sativa

<400> SEQUENCE: 6
ttccgtctct ttcctctctc ttctctctcc ccctctcctg gaggagagag aggagaagag     60
gagggggggc cgcgccaaga gccacgcgcg ctacagtctc cttcccaccc cgcaccgcga    120
gcaatggaga tggccagtgg aggaggcgcc gccgccgccg ccggcggcgg agtaggcggc    180
agcggcggcg gtggtggtgg aggggacgag caccgccagc tgcacggtct caagttcggc    240
aagaagatct acttcgagga cgccgccgcg gcagcaggcg gcggcggcac tggcagtggc    300
agtggcagcg cgagcgccgc gccgccgtcc tcgtcttcca aggcggcggg tggtggacgc    360
ggcggagggg gcaagaacaa ggggaagggc gtggccgcgg cggcgccacc gccgccgccg    420
ccgccgccgc ggtgccaggt ggagggggtgc ggcgcggatc tgagcgggat caagaactac    480
tactgccgcc acaaggtgtg cttcatgcat tccaaggctc cccgcgtcgt cgtcgccggc    540
ctcgagcagc gcttctgcca gcagtgcagc aggttccacc tgctgcctga atttgaccaa    600
```

-continued

| | |
|---|---|
| ggaaaacgca gctgccgcag acgccttgca ggtcataatg agcgccggag gaggccgcaa | 660 |
| acccctttgg catcacgcta cggtcgacta gctgcatctg ttggtgagca tcgcaggttc | 720 |
| agaagcttta cgttggattt ctcctaccca agggttccaa gcagcgtaag gaatgcatgg | 780 |
| ccagcaattc aaccaggcga tcggatctcc ggtggtatcc agtggcacag gaacgtagct | 840 |
| cctcatggtc actctagtgc agtggcggga tatggtgcca acacatacag cggccaaggt | 900 |
| agctcttctt cagggccacc ggtgttcgct ggcccaaatc tccctccagg tggatgtctc | 960 |
| gcagggtcg gtgccgccac cgactcgagc tgtgctatct ctcttctgtc aacccagcca | 1020 |
| tgggatacta ctaccacag tgccgctgcc agccacaacc aggctgcagc catgtccact | 1080 |
| accaccagct ttgatggcaa tcctgtggca ccctccgcca tggcgggtag ctacatggca | 1140 |
| ccaagcccct ggacaggttc tcggggccat gagggtggtg gtcggagcgt ggcgcaccag | 1200 |
| ctaccacatg aagtctcact tgatgaggtg caccctggtc ctagccatca tgcccacttc | 1260 |
| tccggtgagc ttgagcttgc tctgcagggg aacggtccag ccccagcacc acgcatcgat | 1320 |
| cctgggtccg gcagcacctt cgaccaaacc agcaacacga tggattggtc tctgtagagg | 1380 |
| ctgttccagc tgccatcgat ctgtcgtccc gcaaggcgag tcatggaact gaagaacctc | 1440 |
| atgctgcctg cccttatttt gtgttcaaat tttcctttcc agtatggaaa ggaaattcta | 1500 |
| aggtgactgg cgattaatct ccctgtgatg aataataatg cgcgcccttg aactcaatta | 1560 |
| attgctgtgc cgcatccatc tatgtaactc tccatgaatt tttaagtatc agtgttaatg | 1620 |
| ctgt | 1624 |

<210> SEQ ID NO 7
<211> LENGTH: 417
<212> TYPE: PRT
<213> ORGANISM: Oryza sativa

<400> SEQUENCE: 7

Met Glu Met Ala Ser Gly Gly Ala Ala Ala Ala Gly Gly
1               5                   10                  15

Val Gly Gly Ser Gly Gly Gly Gly Gly Gly Asp Glu His Arg Gln
            20                  25                  30

Leu His Gly Leu Lys Phe Gly Lys Lys Ile Tyr Phe Glu Asp Ala Ala
        35                  40                  45

Ala Ala Ala Gly Gly Gly Gly Thr Gly Ser Gly Ser Gly Ser Ala Ser
    50                  55                  60

Ala Ala Pro Ser Ser Ser Lys Ala Gly Gly Gly Arg Gly
65                  70                  75                  80

Gly Gly Gly Lys Asn Lys Gly Lys Gly Val Ala Ala Ala Pro Pro
                85                  90                  95

Pro Pro Pro Pro Pro Arg Cys Gln Val Glu Gly Cys Gly Ala Asp
            100                 105                 110

Leu Ser Gly Ile Lys Asn Tyr Tyr Cys Arg His Lys Val Cys Phe Met
        115                 120                 125

His Ser Lys Ala Pro Arg Val Val Val Ala Gly Leu Glu Gln Arg Phe
    130                 135                 140

Cys Gln Gln Cys Ser Arg Phe His Leu Leu Pro Glu Phe Asp Gln Gly
145                 150                 155                 160

Lys Arg Ser Cys Arg Arg Arg Leu Ala Gly His Asn Glu Arg Arg
                165                 170                 175

Arg Pro Gln Thr Pro Leu Ala Ser Arg Tyr Gly Arg Leu Ala Ala Ser
            180                 185                 190

```
Val Gly Glu His Arg Arg Phe Arg Ser Phe Thr Leu Asp Phe Ser Tyr
        195                 200                 205
Pro Arg Val Pro Ser Ser Val Arg Asn Ala Trp Pro Ala Ile Gln Pro
210                 215                 220
Gly Asp Arg Ile Ser Gly Ile Gln Trp His Arg Asn Val Ala Pro
225                 230                 235                 240
His Gly His Ser Ser Ala Val Ala Gly Tyr Gly Ala Asn Thr Tyr Ser
            245                 250                 255
Gly Gln Gly Ser Ser Ser Gly Pro Pro Val Phe Ala Gly Pro Asn
        260                 265                 270
Leu Pro Pro Gly Gly Cys Leu Ala Gly Val Gly Ala Ala Thr Asp Ser
            275                 280                 285
Ser Cys Ala Ile Ser Leu Leu Ser Thr Gln Pro Trp Asp Thr Thr Thr
290                 295                 300
His Ser Ala Ala Ala Ser His Asn Gln Ala Ala Ala Met Ser Thr Thr
305                 310                 315                 320
Thr Ser Phe Asp Gly Asn Pro Val Ala Pro Ser Ala Met Ala Gly Ser
                325                 330                 335
Tyr Met Ala Pro Ser Pro Trp Thr Gly Ser Arg Gly His Glu Gly Gly
            340                 345                 350
Gly Arg Ser Val Ala His Gln Leu Pro His Glu Val Ser Leu Asp Glu
        355                 360                 365
Val His Pro Gly Pro Ser His His Ala His Phe Ser Gly Glu Leu Glu
    370                 375                 380
Leu Ala Leu Gln Gly Asn Gly Pro Ala Pro Ala Pro Arg Ile Asp Pro
385                 390                 395                 400
Gly Ser Gly Ser Thr Phe Asp Gln Thr Ser Asn Thr Met Asp Trp Ser
                405                 410                 415
Leu

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This sequence may encompass 5-6 residues

<400> SEQUENCE: 8

Arg Arg Arg Arg Arg Arg
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Arg Arg Arg Arg
1               5

<210> SEQ ID NO 10
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(10)
<223> OTHER INFORMATION: This sequence may encompass 2-10 residues

<400> SEQUENCE: 10

His His His His His His His His His His
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His His His His His His
1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Tyr Lys Asp Asp Asp Asp Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Trp Ser His Pro Gln Phe Glu Lys
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Gln Lys Leu Ile Ser Glu Glu Asp Leu
1               5                   10

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 15
aggtaccgca atgtagagcc acgtaggcaa g                              31

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agggcccgct taccagctat tggttacaca tatt                           34

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cggtcgacta gctgcatctg ttgg                                      24

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catcgtgttg ctggtttggt cgaag                                     25

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ccctccacct cgtcctcag                                            19

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
agataacaac ggaagcataa aagtc                                     25

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 21
aggatcccca gccatgggat actactacc                                              29

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aggtacccag cattaacact gatacttaaa                                             30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aactagtcag cattaacact gatacttaaa                                             30

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
agagctccca gccatgggat actactacc                                              29
```

PROTEIN IPA1 RELATED TO PLANT ARCHITECTURE, ITS CODING GENES AND USES

SEQUENCE LISTING

The instant application contains a Sequence Listing which has been submitted electronically in ASCII format and is hereby incorporated by reference in its entirety. Said ASCII copy, created on Nov. 6, 2013, is named 205333-0012-00-US-489273_SL.txt and is 32,224 bytes in size.

FIELD OF THE INVENTION

The invention relates to a field of plant gene engineering technology, specifically relates to a protein IPA1 associated with plant architecture, coding genes and uses thereof.

BACKGROUND OF THE INVENTION

The plant architecture of rice includes traits such as tiller number, tillers angle, panicle type and plant height. A good plant architecture is a key factor to improve the yield of rice. A majority of cultivars for an application in production currently are dwarf varieties containing a semi-dwarf gene SD1. The dwarf varieties have many advantages compared with the traditional long-stalk varieties, thus the first "green revolution" was set off and the yield of rice was largely increased. However, a further increase of the yield was limited by the inherent shortcomings of the dwarf varieties, including more unproductive tillers, smaller panicles and higher leaf area index, serious leaf shading phenomenon and decreased canopy photosynthesis and so on. In order to overcome the disadvantage of the limited yield potential of current most cultivars and further meet the people's demand for foodstuff, the breeders of the International Rice Research Institute proposed the concept of new plant type of rice and the main features of the new plant type were fewer tillers, no unproductive tillers, bigger panicles, more grains per panicle, thick and sturdy stems and lodging resistance.

The tiller number of rice is an important agronomic trait in the rice production. The number of productive tillers per unit area decides the number of panicles, which in turn is one of three critical factors to decide the rice yield per unit area. Thus, the reasonable controlling of the occurrence of rice tillering and minimizing the unproductive tillers are of great importance to production.

The grain number per panicle is another important factor in determining the yield of rice. The typical characteristic of most high-yield varieties used currently in production is the significant increase of grain number per panicle. The increase of grain number per panicle is mainly attributed to more primary rachis branch and secondary rachis branch on the panicles and denser grains grown. It is very important to increase the grain number per panicle in breeding high-yield varieties. The 1000-seed weight is the third critical factor to the yield of rice, which is the direct reflection of good or bad dry matter accumulation and grouting in rice grains and is closely associated with the size of the grains.

The lodging resistance ability is always an aspect to which rice breeders have been attaching great importance. It plays a very important role in stabilizing yield and is a limiting factor to further increase the yield, though it does not directly improve the yield of rice. The dwarf varieties enhance the lodging resistance ability through reducing the plant height and thus ensure the stable production of rice and make it possible to increase the yield, compared with the traditional long-stalk varieties. Further enhancing the lodging resistance ability of the plants therefore is critical to further increasing the yield of rice. In the regard, it is always a goal of the breeders to enhance the traits of stem and to breed a variety whose stems are more thick and sturdy and whose lodging resistance ability is stronger.

The basic characteristics of the new plant type proposed by the International Rice Research Institute are few tillers, thick stems and big panicles. The simulation studies suggested that the yield of the variety with new plant type increased by 25% compared with current varieties in the dry season in the tropical regions. It is important to demonstrate the genetic basis and molecular mechanism of tillering, stems and panicles development for obtaining a higher yield variety. Currently, there is no report on genes which may systematically change the plant type of rice overall to produce new plant type characteristics, though many genes associated with the yield were cloned.

SUMMARY OF THE INVENTION

The object of the invention is to provide a protein associated with plant architecture and coding gene thereof.

The name of the protein associated with plant architecture of invention is IPA1, which originates from rice (*Oryza saliva* L.), as protein shown in the following 1) or 2):

1) a protein consists of amino acid sequence as sequence 1 in the sequence list; and 2) a protein related to plant architecture which derived from amino acid sequence as sequence 1 in the sequence list via substitution and/or missing and/or addition of one or more amino acid residues.

To facilitate the purification of IPA1 in 1), the amino-terminal or carboxyl-terminal of the protein consisting of amino acid sequence as sequence 1 in the sequence list may be added with tags as listed in Table 1.

TABLE 1

| Sequence of Tags | | |
|---|---|---|
| Tags | Residues | Sequences |
| Poly-Arg | 5-6 (typically 5) (SEQ ID NO: 8) | RRRRR (SEQ ID NO: 8) |
| Poly-His | 2-10 (typically 6) (SEQ ID NO: 10) | HHHHHH (SEQ ID NO: 11) |
| FLAG | 8 | DYKDDDDK (SEQ ID NO: 12) |
| Strep-tag II | 8 | WSHPQFEK (SEQ ID NO: 13) |
| c-myc | 10 | EQKLISEEDL (SEQ ID NO: 14) |

IPA1 as described above in 2) may be artificially synthesized; alternatively obtained by expressing its coding gene in organisms. The coding gene of IPA1 as described above in 2) may be achieved through deleting or adding codons for one or more amino acid residues in DNA sequence from 124 to 1377 bp of 5'-end of sequence 2 in the sequence list, and/or through one or more missense mutation of base pair, and/or through adding the tags as listed in Table 1 to 5'-end and/or 3'-end thereof.

The coding gene for the protein associated with plant architecture as described above (denominated as IPA1 gene) is also within the scope of the invention.

The coding gene for the protein associated with plant architecture as described above specifically is one of genes described as following 1)-5):

1) its coding sequence as listed from 124 to 1377 bp of 5'-end of sequence 2 in the sequence list;
2) its nucleotide sequence is sequence 2 in the sequence list;
3) its nucleotide sequence of genetic DNA as listed from 1 to 7229 bp of 5'-end of sequence 3 in the sequence list;
4) a gene which is hybridized with the gene in 1), 2) or 3) under the stringent conditions and codes the said protein; and
5) a gene which has above 90% homology with the gene in 1), 2) or 3) and codes the said protein.

The sequence 2 in the sequence list consists of 1624 bases; its open reading frame (ORF) is from 124 to 1377 base of 5'-end and it codes IPA1 protein having amino acid sequence of sequence 1 in the sequence list.

The stringent conditions as described above may use 0.1× SSPE (or 0.1×SSC) and 0.1% SDS solution, hybridize at 65° C. and wash the membrane in DNA or RNA hybridization assay.

The primers for the amplification of full length IPA1 gene or any portion thereof are also within the scope of the invention.

Expression cassettes, recombinant vectors, transgenic cell lines and recombinant bacteria containing the coding gene for the protein associated with plant type as described above are also within the scope of the invention.

The recombinant expression vector containing IPA1 gene may be constructed using the existing plant expression vectors. The said plant expression vectors include binary *Agrobacterium* vector and vectors for plant bombarding and the like, such as pCAMBIA3301, pCAMBIA1300, pBI1121, pBin19, pCAMBIA2301, pCAMBIA1301-UbiN or other derived plant expression vectors.

Any enhanced promoter, constitutive promoter, tissue-specific promoter or inducible promoter, such as cauliflower mosaic virus (CAMV) 35S promoter and ubiquitin gene promoter (pUbi) and the like, alone or combined with other plant promoters, may be added to the transcription start nucleotide when using IPA1 gene to construct the recombinant expression vector. Additionally, an enhancer may also be used, including a translation enhancer or a transcription enhancer when using the gene of the invention to construct the plant expression vector, these enhancer regions are ATG start code or start code in adjacent region, but they have to be the same as the reading frame of the coding sequence to ensure the correct translation of the whole sequence. The origins of the said translation control signals and start codes are extensive; they may be either natural or synthetic. The translation start region can be derived from transcription start region or structural genes.

To facilitate the identifying and screening of transgenic plant cell or plant, the plant expression vectors used can be modified, such as adding enzymes producing color changing in the expression of plant or genes for luminous compounds (GUS gene, GFP gene and luciferase gene and so on), antibiotic resistance gene (gentamycin resistance, kanamycin resistance and so on) or chemical reagents resistance gene (such as gene for anti-rust agent) and the like.

The said recombinant expression vectors may be specifically a recombinant expression vector that is produced through inserting the coding gene for the protein associated with plant type as described above into the multi-clonal site of the plant expression vector pCAMBIA1300.

Another object of the invention is to provide a method for breeding transgenic plants.

The method for breeding the transgenic plant of the invention comprises introducing the coding gene IPA1 for the protein associated with the plant type as described above or genomic DNA into a plant to produce transgenic plants; the said transgenic plants are of fewer tillers, thick and sturdy stems, more panicles and rachis branches and more grain number per panicle compared with the said target plant.

The said coding gene IPA1 for the protein associated with plant type as described above was introduced into the target plant via the recombinant expression vectors as described above.

The plant expression vectors carrying the coding gene IPA1 for the protein associated with plant type of the invention can be transformed into the plant cells or tissues through conventional biological methods such as Ti plasmid, Ri plasmid, plant virus vectors, direct DNA transformation, microinjection, electrically transduction, *Agrobacterium*-mediated method and so on. The transformed plant hosts (the target plants) are dicotyledon or monocotyledon, preferably rice, more preferably Nipponbare.

Another object of the invention is to provide a method for breeding transgenic plants. The method comprises introducing an interference vector into a target plant to obtain a transgenic plant; the said transgenic plants are of much more tillers, thinner stems, less primary rachis branches and fewer grain numbers per panicle compared with the said target plant; the said interference vector is a recombinant vector achieved through inserting sequentially the nucleotide sequence listed as sequence 4 in the sequence list and the nucleotide sequence listed as sequence 5 in the sequence list into site between BamHI and KpnI and site between SpeI and SacI sites in the vector pTCK303. The target plants are dicotyledon or monocotyledon, preferably rice, more preferably Ri22.

The sequence 4 is a fragment from 1014 bp to 1623 bp of the sequence 2 and the sequence 5 is a reverse complementary sequence to the sequence 4. It was confirmed that there was no other homological sequence with the sequence 4 and 5 in the genome of rice through a whole genome alignment analysis.

A pleiotropic gene IPA1 which can control the tiller number and the development of the stems and panicles was isolated using a map-based cloning method, and the function of the gene was confirmed through a functional complementation experiment.

It was proved by the experiment: the tiller number of the rice was reduced, the stems became thick and sturdy, the number of the panicles and rachis branches were increased and grain number per panicle was improved after the gene of the invention was overexpressed in the rice; the plant height was decreased, the tillers was increased, the stems became thinner and the number of the panicles and rachis branches were reduced after the gene of the invention was loss of function or the activity of the gene was reduced, which suggested that the gene can control the plant architecture of the rice. Thus, the IPA1 gene provides a powerful tool to breed a new plant type rice variety using molecular marker assisted breeding and using genetic engineering method, whereby to further improve the yield of the rice, and this gene has important theoretical significance and great potential for application.

DESCRIPTION OF THE FIGURES

FIGS. 2a and 2b are drawings showing QTL analysis and location using BC$_2$F$_2$. FIG. 2c is a fine location map; a number under a tag represents a recombinant individual; FIG. 2d is a predicted gene within a range of 78 kb, and an arrow represents a predicted gene; FIG. 2e is a schematic diagram of the structure of the IPA1 gene of invention, a white blank box represents 5' and 3' untranslated region, a black box represents an exon, a middle horizontal line represents an intron and a red star represents miRNA156 target site. The change of the bases above the box represents a base mutation in the Shaoniejing materials. The number in the brackets represents the position of the base mutation.

FIG. 3 is sequence diagram of cDNA_(SEQ ID NO: 2) and protein (SEQ ID NO: 1) of the IPA1 gene, the blue nucleotides represent 5' and 3' noncoding region, the protein sequence underlined represents SBP structure domain, a red star represents miRNA156 target site and a red letter represents a nucleotide mutation in the Shaoniejing material and an amino acid change resulted from the mutation.

FIG. 4a is giPA1 vector map; FIG. 4b is the phenotype of the gIPA1 transgenic rice; FIG. 4c is the expression level of IPA1 determined by RT-PCR; FIG. 4d is the statistical comparisons of the agronomic traits associated with gIPA1 transgenic materials via T test, a single-star represents significant and a double-star represents very significant; Nipponbare is wild type control and gIPA1 is the transgenic plant in FIGS. 4b, 4c and 4d.

FIG. 5a is the phenotype of the transgenic rice obtained with RNA interference; FIG. 5b is the expression level of IPA1 in the transgenic plant determined by RT-PCR; FIG. 5c is the comparisons of the agronomic traits associated with the transgenic rice obtained with RNA interference via T test and a double-star represents very significant; Ri 22 is non-transgenic control and IPA1-RNAi is the transgenic plant in FIGS. 5a, 5b and 5c.

EMBODIMENTS OF THE INVENTION

The following embodiments are presented to further illustrate the invention, but the invention is not limited to the examples.

The methods in the following examples are all conventional methods, unless otherwise indicated.

The rice in the following examples was obtained through a cultivation method as follows: (1) field cultivation of the rice materials: The rice seeds were soaked in the water for 2 days, and then were transferred into a culture room at 37° C. to accelerate the germination of the seeds for 3 days, the seeds showing white were then seeded into a seedbed to raise rice seedlings and the rice seedlings were transplanted into a paddy field when the seedlings had 4 leaves.

Example 1

The Discovery of the Gene

Figure 1:
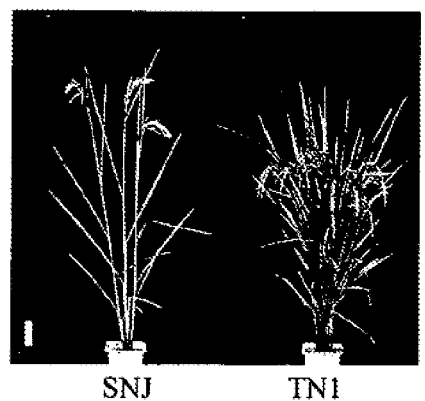
FIG. 1 shows a phenotype of rice materials, including Shaoniejing (SNJ) with fewer tillers and conventional indica rice variety TN1.

The seeds of Shaoniejing with fewer tillers, sturdier stems and big panicles and conventional indica rice variety TN1 of rice (*Oryza sativa* L.) were grown according to the field cultivation method as described above and the morphology of the mature plant was shown in FIG. 1. The DNA was extracted from the leaf.

Extraction of Rice Genomic DNA:

The genomic DNA was extracted using the adapted CTAB method (Mou Z, He Y, Dai Y, et al. Deficiency in fatty acid synthase leads to premature cell death and dramatic alterations in plant morphology. The Plant Cell. 2000, 12, 405-418.) from the leaf of rice. 100 mg leaves of the rice was collected and frozen in liquid nitrogen and milled into powder in a small mortar with 5 cm diameter, transferred into a 1.5 ml centrifuge tube to extract DNA and the achieved DNA was dissolved into 100µ MQ H$_2$O.

The map-based cloning was performed according to the steps as follows:

1. Primary Mapping of the IPA1 Gene

Figure 2:
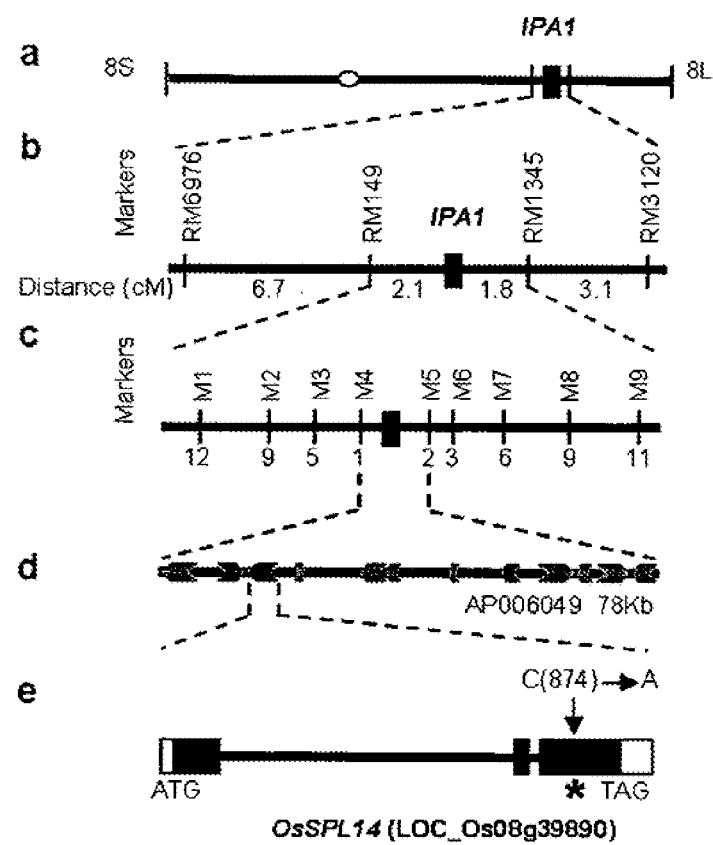
FIG. 2 is map-based cloning of the IPA1 gene.

To isolate the IPA41 gene, a mapping population was firstly constructed using Shaoniejing and TN1. And then the QTL analysis and mapping was performed using BC$_2$F$_2$ individual of the segregating population. The result of the mapping showed that IPA1 was primarily mapped between two markers RM149 and RM1345 at chromosome 8 and the genetic distance was 2.1 cM and 1.8 cM respectively (FIGS. 2a and 2b).

2. Fine Mapping of the IPA1 Gene

To further narrow the definite region of the target gene, 5500 individual plants whose phenotype type was close to TN1 were selected from BC$_2$F$_2$ segregating population to perform the fine mapping. At the same time, a difference site was searched within mapping region through genome sequence between *Indica* rice and *Japonica* rice using 93-11 and Nipponbare published to exploit new STS and SSR makers. An individual plant whose gene was exchanged with that of the target gene was screened firstly using markers RM149 and RM1345 and then these exchanged individual plants were screened using a new molecule marker to find that the molecule markers M3 and M6 were closely linked to the target gene when the fine mapping was performed. There were 5 and 3 recombinants identified respectively. Finally, IPA1 locus was finely mapped in a section of approximately 78 kb between markers M4 and M5 (FIGS. 2c and 2d).

3. Identification and Sequence Analysis of Candidate Genes

A candidate gene prediction was performed on the 78 kb section and a sequence alignment was conducted between TN1 and Shaoniejing materials. The result showed that one point mutation from C to A occurred in the third exon of gene OsSPL14 (LOC_0s08g39890) in the Shaoniejing materials. However, there is no mutation in the same region of Nipponbare and Zhonghua11 and the like. We found that the mutation position was located at the target site of miRNA156 and thus it may affect regulation of miRNA156 on OsSPL14 (FIG. 2e) through an in-depth analysis. Based on the information as above, the gene was determined as a candidate gene. There is a corresponding full-length cDNA sequence AK107191 of the candidate gene in KOME database. An analysis of the protein sequence showed that the candidate gene contained a conserved SBP (SQUAMOSA promoter binding protein) domain (FIG. 3).

Example 2

Acquisition and Testing of the Transgenic Plants

1. Acquisition of the Transgenic Plants
  (1) Construction of a Recombinant Expression Vector
  (a) Cloning of the Genes A DNA fragment comprising the IPA1 gene (The sequencing showed that the nucleotide sequence of the preparatory fragment was listed as sequence 3 in the sequence list) was amplified from the genomic DNA of Nipponbare (The public can obtain the material from Institute of Genetics and Developmental Biology, Chinese Academy of Science and the material was reported in a non-patent literature Lin H, Wang R, Qian Q, et al. DWARF27, an iron-containing protein required for the biosynthesis of strigolactones, regulated rice tillers bud outgrowth. Plant Cell 2009, 21, 1512-1525.). The preparatory fragment was digested with Kpn I and Xba I to obtain a final genomic DNA fragment comprising the full-length IPA1 (The nucleotide sequence was listed as 1-7229 bp from 5'-end of sequence 3 in the sequence list).

In the genomic DNA listed as 1 bp to 7229 bp of sequence 3, 1118 bp to 1566 bp is the first exon, 1567 bp to 3996 bp was the first intron, 3997 bp to 4130 bp was the second exon, 4131 bp to 4232 bp was the second intron and 4233 bp to 4903 bp was the third exon.

The nucleotide sequence of cDNA corresponding to the genomic DNA listed as 1 bp to 7229 bp of sequence 3 is shown as sequence 2 in the sequence list. The sequence 2 consists of 1624 bp; its open reading frame (ORF) is from 124 to 1377 base of 5'-end and it codes IPA1 protein having amino acid sequence of sequence 1 in the sequence list.

TABLE 2

Sequence of the primers

| Name of the primers | Sequence of the primers (5'-3') |
|---|---|
| gIPA11F | AGGTACCGCAATGTAGAGCCACGTAGGCAAG (SEQ ID NO: 15) |
| gIPA11R | AGGGCCCGCTTACCAGCTATTGGTTACACATATT (SEQ ID NO: 16) |

A Kpn I enzyme cutting site was added into 5'-end of the primer gIPA11F and an Apa I enzyme cutting site was added into 5'-end of primer gIPA11R.

(b) Construction of the Expression Vector

The final genomic DNA fragment comprising the full-length IPA1 gene obtained in step (a) was inserted into a site between Kpn I and Xba I sites of vector pCAMBIA1300 (commercially available from Cambia company) to achieve a recombinant expression vector gIPA1 (FIG. 4a) and it was confirmed that the construction was correct.

(2) Acquisition of the Transgenic Plants

The gIPA1 plasmid was transformed into *Agrobacterium tumefaciens* line EHA05 (The public can obtain the material from Institute of Genetics and Developmental Biology, Chinese Academy of Science and the material was reported in a non-patent literature Lin H, Wang R, Qian Q, et al. DWARF27, an iron-containing protein required for the biosynthesis of strigolactones, regulated rice tillers bud outgrowth. Plant Cell 2009, 21, 1512-1525) through electroporation to screen recombinant *Agrobacterium tumefaciens* strains containing the recombinant plasmid gIPA1.

The callus of Nipponbare was infected with the recombinant *Agrobacterium tumefaciens* strains containing the recombinant plasmid gIPA1, cultured at 25° C. in the darkness for 3 days and resistant callus and transgenic plants were screened on a selective medium containing 50 mg/L hygromycin. The hygromycin resistant plants were acclimated in the shade and transplanted into a paddy field to obtain a transgenic plant $T_0$-generation. The seeds of $T_0$-generation plant were recovered and cultured according to the field cultivation method as described above and T1 transgenic plants with transformed gIPA1 were obtained through the conventional molecular detection.

Nipponbare was transformed with empty vector pCAMBIA1300 to obtain empty vector control plants according to the method of obtaining the T1 transgenic plants with transformed gIPA1.

Figure 4:
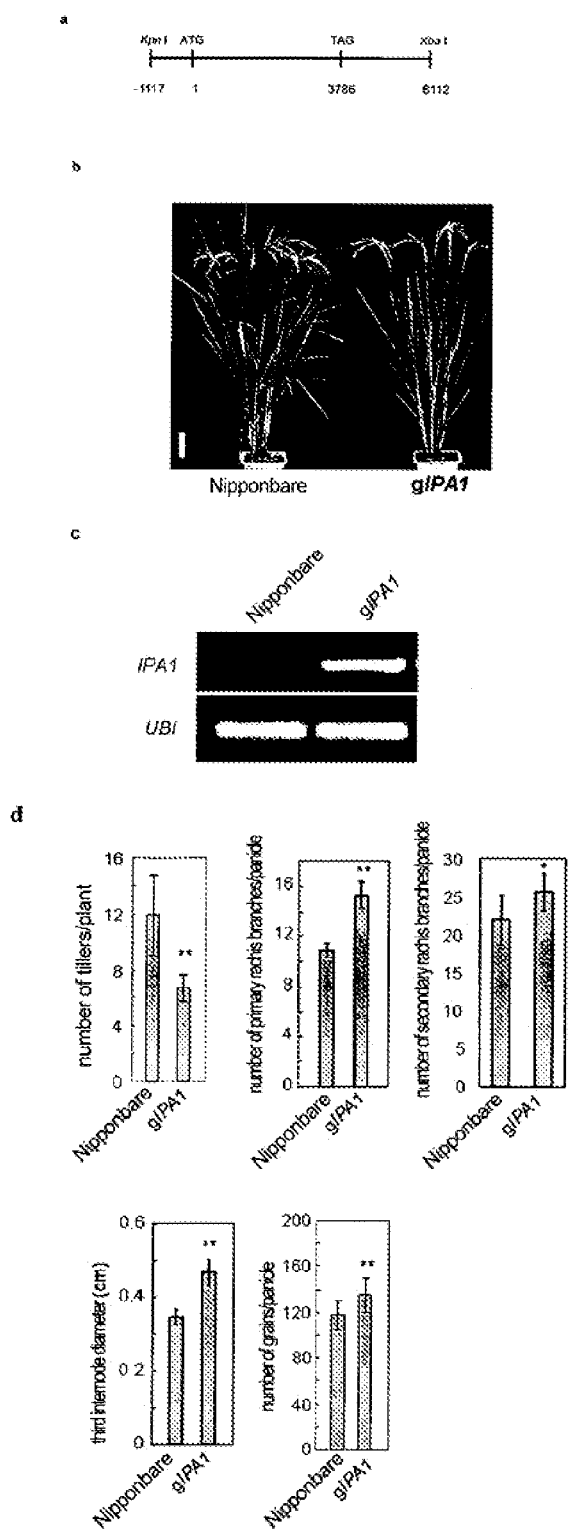
FIG. 4 is gIPA1 vector map and the statistical analysis of phenotype and agronomic traits of the transgenic rice in the functional complementation experiment.

2. Plant Type Characterization of the Transgenic Plants (1) Detecting the Expression Level of the IPA1 Gene Through RT-PCR The total RNA of the plants was extracted from the transgenic plants and the control Nipponbare plants by using TRIZOL (commercially available from Invitrogen Company) and a reverse transcription was performed by using reverse transcription kit (commercially available from Promega Company) to obtain cDNA. The expression of the IPA1 gene was detected through PCR by using primers IPA1RT1F and IPA1RT1R (The sequence of amplified fragment was from 681 bp to 1362 bp region of 5'-end of sequence 2). The Ubiquitin gene was amplified as internal standard by using primers UbiRTF and UbiRTR and the sequence of the primers was listed in Table 3. The results showed that the expression level of IPA1 was increased in transgenic plants (FIG. 4c).

TABLE 3

The sequence of the primers

| Name of the primers | Sequence of the primers (5'-3') |
|---|---|
| IPA1RT1F | CGGTCGACTAGCTGCATCTGTTGG (SEQ ID NO: 17) |
| IPA1RT1R | CATCGTGTTGCTGGTTTGGTCGAAG (SEQ ID NO: 18) |
| UbiRTF | CCCTCCACCTCGTCCTCAG (SEQ ID NO: 19) |
| UbiRTR | AGATAACAACGGAAGCATAAAAGTC (SEQ ID NO: 20) |

(2) Plant Type Characterization of the Transgenic Plants

A statistical analysis of plant type was performed on the $T_1$ transgenic plants with transformed gIPA1, Nipponbare control plants and empty vector control plants, and 10 individual plants were taken from each material. The results were shown in FIGS. 4b and 4d (The phenotype of the empty vector control plants was the same as Nipponbare control plants in FIGS. 4b and 4d, not shown in Figure), which the number of the tillers was reduced (from 11.9 to 6.7 in average), the number of primary rachis branch was significantly increased (from 10.8 to 15.5 in average), the number of secondary rachis branch was also significantly increased (from 21.9 to 25.6 in average), the stems became thicker (the diameter of the third branches was increased from 0.35 cm to 0.47 cm in average) and the grain number per panicle was significantly increased (from 117.1 to 135.7 in average) when the T1 transgenic plants transformed with gIPA1 were compared with plants transformed with the empty vector and Nipponbare.

Example 3

Acquisition and Testing of the Transgenic Plants

1. Acquisition of the Transgenic Plants (1) Obtaining the Interference Fragment

PCR amplification was performed by using primer pair RNA1F/RNAi1R and primer pair RNAi2F/RNAi2R in Table 4 and using KOME full-length cDNA clone (No. AK107191) as template (commercially available from Genome Resource Center, National Institute of Agrobiological Science, Japan), and sequencing was performed on the resulting product. The nucleotide sequence of the gene fragment obtained through the amplification by using these two pairs of primers were shown in sequence 4 and sequence 5 in sequence list respectively.

TABLE 4

The sequence of the primers

| Name of the primers | Sequence of the primers (5'-3') |
|---|---|
| RNAi1F | AGGATCCCCAGCCATGGGATACTACTACC (SEQ ID NO: 21) |
| RNAi1R | AGGTACCCAGCATTAACACTGATACTTAAA (SEQ ID NO: 22) |
| RNAi2F | AACTAGTCAGCATTAACACTGATACTTAAA (SEQ ID NO: 23) |
| RNAi2R | AGAGCTCCCAGCCATGGGATACTACTACC (SEQ ID NO: 24) |

Recognition sites for BamHI and KpnI were added to the 5' end of forward and reverse primer of RNAil respectively and recognition sites for SpeI and SacI were added to the 5' end of forward and reverse primer of RNAi2 respectively.

Sequence 4 is a fragment from 1014 bp to 1623 bp of the sequence 2 and sequence 5 is a reverse complementary sequence of the sequence 4. It was confirmed that there was no other homological sequence with sequence 4 and 5 in the genome of rice through a whole genome alignment analysis.

(2) Construction of the Interference Vector

The product amplified by using primer pair RNAi1F/RNAi1R was cut with BamHI and KpnI and BamHI and KpnI sites of vector pTCK303 carrying Ubiquitin promoter (The public can obtain the material from Institute of Genetics and Developmental Biology, Chinese Academy of Science and the material was reported in a non-patent literature Wand Z, Chen C, Xu Y, et al. A practical vector for efficient knockdown of gene expression in rice (Oryza sativa L.). Plant Mol. Biol. Rep. 2004, 22, 409-417) were inserted to obtain vector 1; the product obtained through amplification by using primer pair RNAi2F/RNAi2R was cut with SpeI and SacI, and the resulting fragments were inserted into the vector to achieve SpeI and SacI sites of vector 1 and then a recombinant expression vector was obtained (ie. interference vector IPA1-RNAi). The fragments inserted formed a hairpin structure after expression.

(3) Acquisition of the Transgenic Plants

The interference vector IPA1-RNAi was transformed into Agrobacterium tumefaciens line EHA05 through electrical bombardment method to screen recombinant Agrobacterium tumefaciens strains which contains the interference vector IPA41-RNAi.

The mature seeds of materials Ri22 containing point mutated gene were shelled, sterilized and sowed into a calli induction medium. The callus was grown from the scutellum after three-week culture. The embryonic callus with vigorous growth, light yellow and loose was selected to use as a receptor of transformation.

The callus of Ri22 rice was infected with the recombinant Agrobacterium tumefaciens strains which contains the interference vector IPA1-RNAi and then cultured at 25° C. in the darkness for 3 days and resistant callus and transgenic plants were screened on a selective medium which contains 50 mg/L hygromycin. The hygromycin resistant plants were acclimated in the shade and then transplanted into a paddy field to obtain a transgenic plant $T_0$ generation. The transgenic seeds of $T_0$ generation were recovered and then cultured to obtain T1 generation transgenic plants with transformed gIPA1.

Ri22 was transformed with empty vector pTCK303 to obtain an empty vector control plant according to the method of obtaining the T1 generation transgenic plants transformed with IPA1-RNAi.

Figure 5:
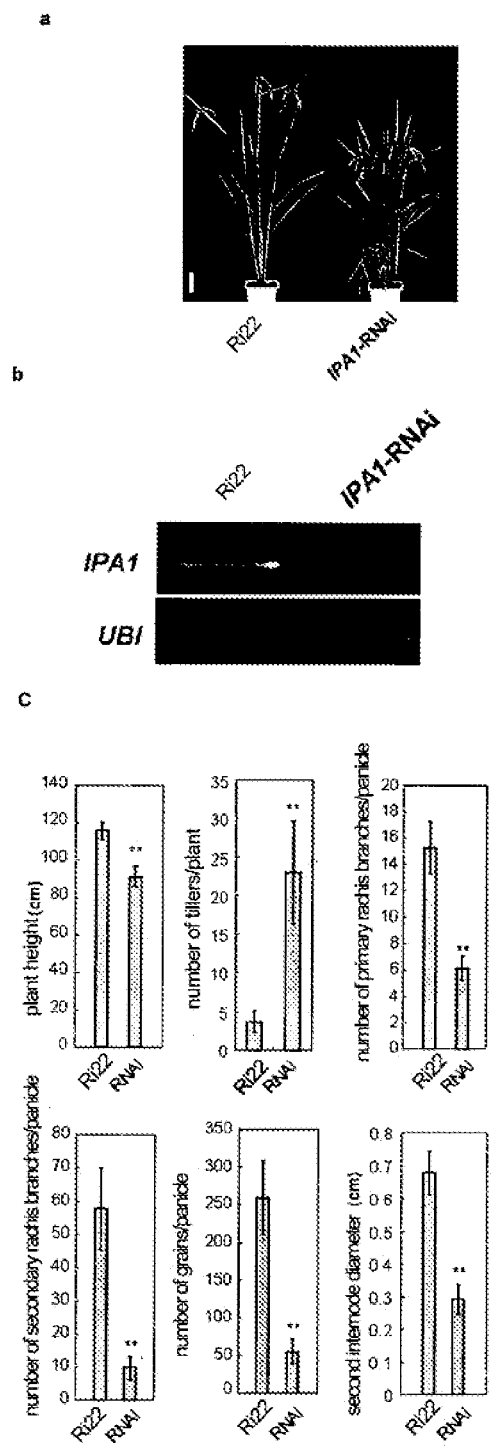
FIG. 5 is the comparison of the phenotype and agronomic traits of the transgenic rice obtained with RNA interference.

2. Detection of the Transgenic Plants (1) Detecting the Expression Level of the IPA1 Gene Through RT-PCR The total RNA of the plants was extracted from the transgenic plants and the control Ri22 plants by using TRIZOL (commercially available from Invitrogen Company) and a reverse transcription was performed by using reverse transcription kit (commercially available from Promega Company) to obtain cDNA. The expression of the IPA1 gene was detected through PCR by using primers IPA1RT1F and IPA1RT1R. Ubiquitin gene was amplified as internal standard by using UbiRTF and UbiRTR and the sequence of the primers was listed in Table 3. The result showed that the expression level of the IPA1 was decreased in the transgenic plants (FIG. 5b).

(2) Plant Type Detection of the Transgenic Plants

A statistics of plant type was performed on the $T_1$ generation transgenic plants with transformed IPA1-RNAi, Ri22 control plants and empty vector control plants and 10 individual plants were taken from each material. The results were shown in FIGS. 5a and 5c (The phenotype of the empty vector control was the same as Nipponbare control in FIGS. 5a and 5c, not shown in Figure), which the plant height was reduced (from 115.7 cm to 91.2 cm in average), the number of the tillers was dramatically increased (from 3.7 to 23.3 in average), the number of primary rachis branch was significantly decreased (from 15.2 to 6.2 in average), the number of secondary rachis branch was also significantly decreased (from 57.5 to 9.7 in average), the grain number per panicle was significantly decreased (from 259.6 to 54.6 in average) and the stems became thinner (the diameter of the second branches was decreased from 0.68 cm to 0.29 cm in average) when the T1 transgenic plants with transformed IPA1-RNAi were compared with the empty vector control plants and Ri22 control.

The invention claimed is:

1. A method of breeding a transgenic plant comprising introducing an interference vector into a target plant to obtain the transgenic plant having changed phenotypes compared with the target plant, wherein the interference vector is constructed by sequentially inserting a first nucleic acid comprising the nucleotide sequence of SEQ ID NO: 4 and a second nucleic acid comprising the nucleotide sequence of SEQ ID NO: 5 into a vector thereby allowing the formation of a hairpin structure upon expression; and wherein the changed phenotypes comprise reduced height, more tillers, thinner stems, fewer primary rachis branches, and fewer grains per panicle.

2. The method of claim 1, wherein the vector is pTCK303, wherein the first nucleic acid is inserted between BamHI and KpnI sites, and wherein the second nucleic acid is inserted between SpeI and SacI sites.

3. The method of claim 1, wherein the plant is a monocotyledon.

4. The method of claim 3, wherein the plant is rice.

* * * * *